(12) United States Patent
Deehr et al.

(10) Patent No.: US 8,585,445 B2
(45) Date of Patent: Nov. 19, 2013

(54) APPARATUS AND METHOD FOR ATTACHING A HEADER TO A HOUSING OF AN IMPLANTABLE DEVICE

(75) Inventors: Mark G. Deehr, Woodinville, WA (US); Michael J. Kloosterboer, Minneapolis, MN (US); Blair Erbstoeszer, Kirkland, WA (US); David A. Chizek, Brooklyn Park, MN (US); Mee S. Burckhardt, Redmond, WA (US); Noel Doherty, Co Limerick (IE); John M. Edgell, Plymouth, MN (US); Lawrence D. Swanson, White Bear Lake, MN (US); John E. Hansen, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/207,918

(22) Filed: Aug. 11, 2011

(65) Prior Publication Data

US 2012/0052710 A1    Mar. 1, 2012

Related U.S. Application Data

(60) Provisional application No. 61/376,785, filed on Aug. 25, 2010.

(51) Int. Cl.
*H01R 13/625* (2006.01)
(52) U.S. Cl.
USPC ............................. 439/669; 439/345; 607/36
(58) Field of Classification Search
USPC ............................. 439/669, 345, 347; 607/37
See application file for complete search history.

(56) References Cited

U.S. PATENT DOCUMENTS

| | | | | | |
|---|---|---|---|---|---|
| 2,569,037 | A | * | 9/1951 | Dalton | 439/368 |
| 2,866,958 | A | * | 12/1958 | Postell | 439/709 |
| 3,683,932 | A | * | 8/1972 | Cole | 607/37 |
| 3,760,332 | A | * | 9/1973 | Berkovits et al. | 439/381 |
| 4,056,299 | A | * | 11/1977 | Paige | 439/439 |
| 4,109,987 | A | * | 8/1978 | Bourdon | 439/372 |
| 4,142,532 | A | * | 3/1979 | Ware | 607/37 |
| 4,182,345 | A | * | 1/1980 | Grose | 607/37 |
| 4,226,244 | A | * | 10/1980 | Coury et al. | 607/37 |

(Continued)

FOREIGN PATENT DOCUMENTS

| | | |
|---|---|---|
| EP | 0004783 A2 | 10/1979 |
| EP | 1417986 A1 | 5/2004 |
| WO | WO-2009/009298 A1 | 1/2009 |
| WO | WO-2012027126 A1 | 3/2012 |

OTHER PUBLICATIONS

"International Application Serial No. PCT/US2011/047415, International Search Report mailed Oct. 10, 2011", 4 pgs.

(Continued)

*Primary Examiner* — Amy Cohen Johnson
*Assistant Examiner* — Vladimir Imas
(74) *Attorney, Agent, or Firm* — Schwegman Lundberg & Woessner, P.A.

(57) ABSTRACT

An apparatus includes an implantable housing, a header including a cavity, a post extending from a surface of the housing into the cavity, the post including an expanded head portion, and a retaining member mounted within the header and engaged with the post with a bottom surface of the retaining member abutting an internal surface of the header.

20 Claims, 6 Drawing Sheets

(56) References Cited

U.S. PATENT DOCUMENTS

| | | | | |
|---|---|---|---|---|
| 4,254,775 A * | 3/1981 | Langer | | 607/5 |
| 4,445,511 A * | 5/1984 | Cowdery et al. | | 607/37 |
| 4,498,405 A * | 2/1985 | Hanyu et al. | | 112/168 |
| 4,715,380 A * | 12/1987 | Harris | | 607/37 |
| 4,854,898 A * | 8/1989 | Turk | | 439/723 |
| 4,934,366 A * | 6/1990 | Truex et al. | | 607/37 |
| 4,980,800 A * | 12/1990 | Furuta | | 361/727 |
| 5,106,321 A * | 4/1992 | Haroutel | | 439/310 |
| 5,149,279 A * | 9/1992 | Kruse | | 439/441 |
| 5,242,373 A * | 9/1993 | Scott et al. | | 600/7 |
| 5,261,395 A * | 11/1993 | Oleen et al. | | 607/15 |
| 5,314,451 A * | 5/1994 | Mulier | | 607/33 |
| 5,366,315 A * | 11/1994 | Hartley | | 403/326 |
| 5,426,831 A * | 6/1995 | Leonelli, Jr. | | 24/459 |
| 5,431,582 A * | 7/1995 | Carvalho et al. | | 439/372 |
| 5,595,498 A * | 1/1997 | Jego et al. | | 439/342 |
| 5,620,477 A * | 4/1997 | Pless et al. | | 607/37 |
| 5,641,299 A * | 6/1997 | Meguro et al. | | 439/347 |
| 5,791,932 A * | 8/1998 | Hasenfratz | | 439/347 |
| 5,823,812 A * | 10/1998 | Bhargava et al. | | 439/345 |
| 5,871,514 A | 2/1999 | Wiklund et al. | | |
| 5,951,595 A * | 9/1999 | Moberg et al. | | 607/37 |
| 6,033,250 A * | 3/2000 | Pauza | | 439/357 |
| 6,205,358 B1 * | 3/2001 | Haeg et al. | | 607/36 |
| 6,398,574 B1 * | 6/2002 | Biermann et al. | | 439/350 |
| 6,520,791 B2 * | 2/2003 | Burger | | 439/362 |
| 6,520,812 B1 * | 2/2003 | Machado | | 439/855 |
| 6,574,508 B2 * | 6/2003 | Zaouali et al. | | 607/36 |
| 6,738,672 B2 * | 5/2004 | Schulman et al. | | 607/116 |
| 6,752,668 B2 * | 6/2004 | Koch, Jr. | | 439/843 |
| 6,911,000 B2 * | 6/2005 | Mick et al. | | 600/7 |
| 7,155,283 B2 * | 12/2006 | Ries et al. | | 607/37 |
| 7,167,749 B2 * | 1/2007 | Biggs et al. | | 607/36 |
| 7,187,974 B2 * | 3/2007 | Haeg et al. | | 607/36 |
| 7,191,009 B2 * | 3/2007 | Laske et al. | | 607/37 |
| 7,231,253 B2 * | 6/2007 | Tidemand et al. | | 607/37 |
| 7,257,445 B2 | 8/2007 | Bruchmann et al. | | |
| 7,345,891 B2 * | 3/2008 | Barsun et al. | | 361/803 |
| 7,628,651 B2 * | 12/2009 | Yeh | | 439/607.37 |
| 7,632,148 B1 * | 12/2009 | Kawamura et al. | | 439/607.41 |
| 7,684,201 B2 * | 3/2010 | Bailey et al. | | 361/741 |
| 7,690,687 B2 * | 4/2010 | Reid et al. | | 280/784 |
| 7,883,375 B2 * | 2/2011 | Li et al. | | 439/620.24 |
| 7,955,111 B2 * | 6/2011 | Costabel et al. | | 439/287 |
| 7,988,485 B2 * | 8/2011 | Zhang et al. | | 439/372 |
| 8,128,330 B2 * | 3/2012 | Zeytoonian | | 411/372.5 |
| 8,138,872 B2 * | 3/2012 | Yoshihara et al. | | 335/281 |
| 8,172,625 B2 * | 5/2012 | Kashiwada et al. | | 439/848 |
| 8,313,336 B2 * | 11/2012 | Bondo et al. | | 439/324 |
| 2003/0040780 A1 * | 2/2003 | Haeg et al. | | 607/36 |
| 2003/0045911 A1 * | 3/2003 | Bruchmann et al. | | 607/36 |
| 2004/0116976 A1 * | 6/2004 | Spadgenske | | 607/37 |
| 2004/0122481 A1 * | 6/2004 | Tidemand et al. | | 607/37 |
| 2011/0226209 A1 * | 9/2011 | Zurface et al. | | 123/90.44 |
| 2012/0088387 A1 * | 4/2012 | Walker et al. | | 439/304 |

OTHER PUBLICATIONS

"International Application Serial No. PCT/US2011/047415, Written Opinion mailed Oct. 10, 2011", 6 pgs.

"International Application Serial No. PCT/US2011/047415, International Preliminary Report on Patentability mailed Mar. 7, 2013", 7 pgs.

* cited by examiner

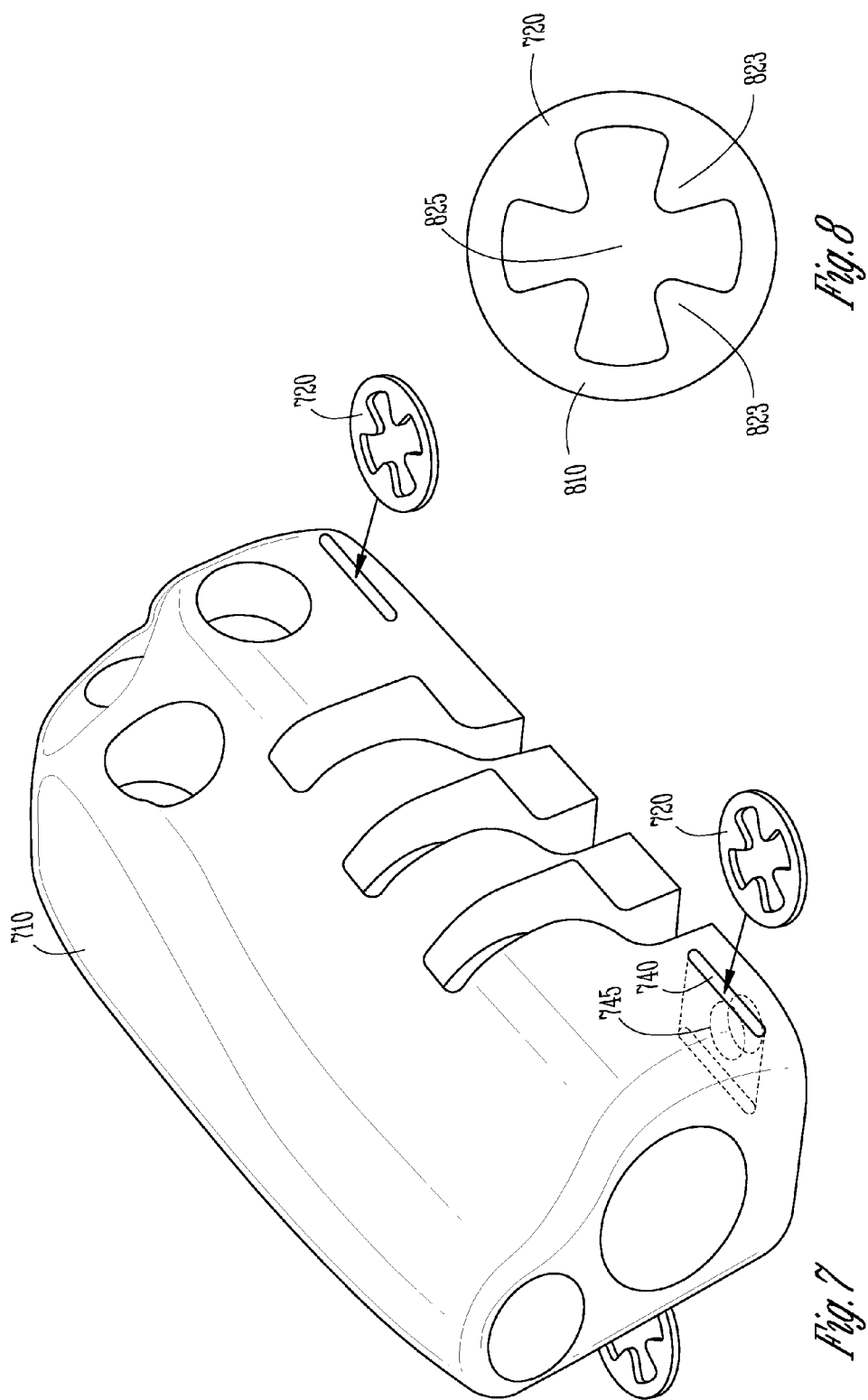

APPARATUS AND METHOD FOR ATTACHING A HEADER TO A HOUSING OF AN IMPLANTABLE DEVICE

CROSS-REFERENCE TO RELATED APPLICATIONS

This application claims the benefit of U.S. Provisional Application No. 61/376,785, filed on Aug. 25, 2010, under 35 U.S.C. §119(e), which is incorporated herein by reference in its entirety.

BACKGROUND

Implantable devices such as pacemakers or defibrillators include a housing and an attached header. The header includes one or more ports to receive a terminal end of an implantable lead. The ports include contacts that electrically communicate with terminal contacts on the lead. Typically, the header is attached to the housing using medical adhesive. U.S. Pat. No. 7,257,445 discusses a header attached to a housing using a pin and bracket configuration.

As implantable devices become smaller, it is becoming more difficult to robustly attach the header to the housing since the usable surface area is so small. Also, ease of manufacturability of the attachment technique is a factor.

OVERVIEW

The present inventors have recognized, among other things, a need for an apparatus that can include an implantable housing, a header including a cavity, a post extending from a surface of the housing into the cavity, the post including an expanded head portion, and a retaining member mounted within the header and engaged with the post with a bottom surface of the retaining member abutting an internal surface of the header.

Example 1 can include subject matter that can include an apparatus comprising: an implantable housing; a header including a cavity; a post extending from a surface of the housing into the cavity, the post including an expanded head portion; and a retaining member mounted within the header and engaged with the post with a bottom surface of the retaining member abutting an internal surface of the header.

In Example 2, the subject matter of Example 1 can optionally comprise the retaining member including an external retaining ring.

In Example 3, the subject matter of any of Examples 1-2 can optionally comprise the external retaining ring including an E-ring.

In Example 4, the subject matter of any of Examples 1-3 can optionally comprise the external retaining ring including a push-on ring with internal teeth.

In Example 5, the subject matter of any of Examples 1-4 can optionally comprise a second post, wherein the first post and the second post have different heights.

In Example 6, the subject matter of any of Examples 1-5 can optionally comprise the post being formed of a metallic material and the retaining member being formed of a metallic material and the metallic material of the post being harder than or equal to the hardness of the metallic material of the retaining member.

In Example 7, the subject matter of any of Examples 1-6 can optionally comprise a top surface of the retaining member abutting a bottom surface of the expanded head portion.

In Example 8, the subject matter of any of Examples 1-7 can optionally comprise the post including external threads.

In Example 9, the subject matter of any of Examples 1-8 can optionally comprise the header including a slot extending perpendicular with and communicating with the cavity such that the retaining ring is located within the slot to engage the post.

Example 10 can comprise, or can optionally be combined with the subject matter of any of Examples 1-9 to optionally comprise, an apparatus comprising: an implantable housing; a header including one or more ports for receiving a terminal of a medical lead, the header further including a cavity in a bottom surface of the header and a slot in a side surface of the header, where the slot is perpendicular to the cavity and communicates with the cavity; a post extending from an upper surface of the implantable housing, the post extending into the cavity, the post including an expanded head portion; and a retaining member located within the slot of the header, the retaining member being engaged to the post such that a top surface of the retaining member abuts a bottom surface of the expanded head portion and a bottom surface of the retaining member abutting an internal surface of the header such that the retaining member holds the header against the implantable housing.

In Example 11, the subject matter of any of Examples 1-10 can optionally comprise the retaining member including an external retaining ring.

In Example 12, the subject matter of any of Examples 1-11 can optionally comprise the external retaining ring including an E-ring.

In Example 13, the subject matter of any of Examples 1-12 can optionally comprise the external retaining ring including a push-on ring with internal teeth.

In Example 14, the subject matter of any of Examples 1-13 can optionally comprise the post including external threads.

In Example 15, the subject matter of any of Examples 1-14 can optionally comprise a second post extending from the upper surface of the implantable housing, wherein the first post and the second post have different heights.

Example 16 can comprise, or can optionally be combined with the subject matter of any of Examples 1-15 to comprise a method that can include: inserting a post attached to an implantable housing into a cavity on a header; and mounting a retaining member to the post, with the retaining member inhibiting movement of the header away from the implantable housing.

In Example 17, the subject matter of any of Examples 1-16 can optionally comprise the retaining member including an external retaining ring.

In Example 18, the subject matter of any of Examples 1-17 can optionally comprise the external retaining ring including an E-ring.

In Example 19, the subject matter of any of Examples 1-18 can optionally comprise the external retaining ring including a push-on ring with internal teeth.

In Example 20, the subject matter of any of Examples 1-19 can optionally comprise the retaining member being mounted to the post such that a top surface of the retaining member abuts a bottom surface of an expanded head portion of the post and a bottom surface of the retaining member abuts an internal surface of the header.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7 shows a perspective view of a header in accordance with one example.

FIG. 8 shows a top view of a retaining member, in accordance with one example.

DETAILED DESCRIPTION

Figure 1:
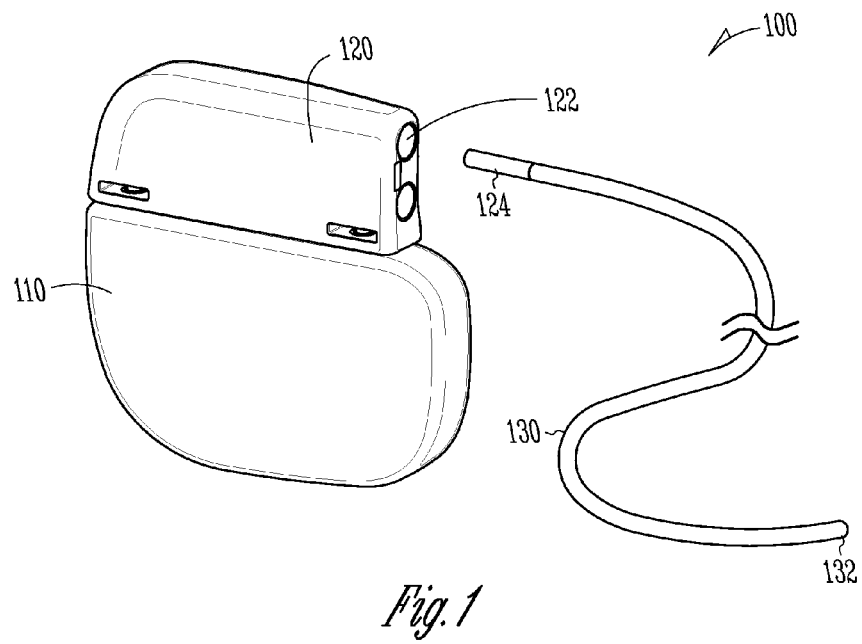
FIG. 1 shows an implantable medical device in accordance with one example.

FIG. 1 shows an implantable medical device 100 in accordance with one example. The implantable medical device 100 includes a metallic housing 110 and an attached header 120. The header 120 includes one or more ports 122 to receive a terminal pin 124 of an implantable lead 130. The lead 130 is configured to deliver pacing pulses, defibrillation shock energy, or cardioversion therapy to a heart, for example. The implantable medical device 100 can be implanted in a surgically-formed pocket in a patient's chest or other desired location. The implantable medical device 100 generally includes electronic components to perform signal analysis, processing, and control. The implantable medical device 100 can include a power supply such as a battery, a capacitor, and other components housed within housing 110. The implantable medical device 100 can include microprocessors to provide processing and evaluation to determine and deliver electrical shocks and pulses of different energy levels and timing for ventricular defibrillation, cardioversion, and pacing to a heart in response to cardiac arrhythmia including fibrillation, tachycardia, and bradycardia via one or more electrodes 132 of the lead 130.

Figure 2:
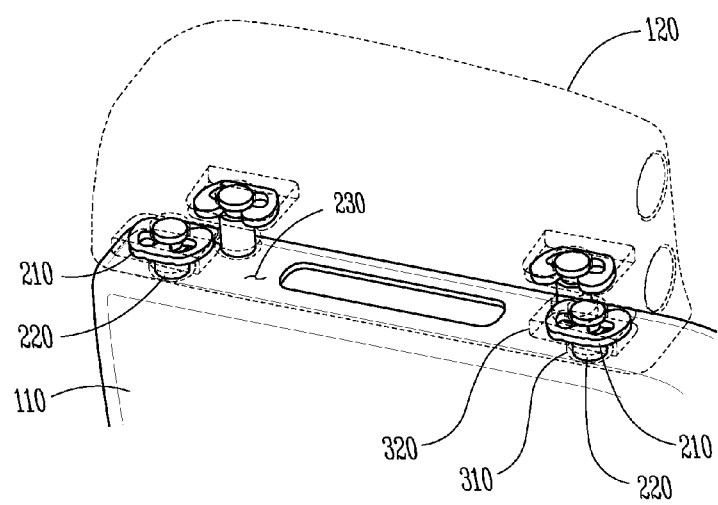
FIG. 2 shows a perspective, internal view of a housing and a header of an implantable medical device, in accordance with one example.

FIG. 2 shows a perspective, internal view of the header 120 mounted to the housing 110. As will be further explained below, the header 120 is physically mounted to the housing 110 by one or more retaining members 210 mounted to one or more respective posts 220 that are attached to a top surface 230 of the housing 110 and mounted within cavities 310 of the header 120. The retaining members 210 provide for a rigid mechanical connection of the header 120 to the housing 110.

Figure 3:
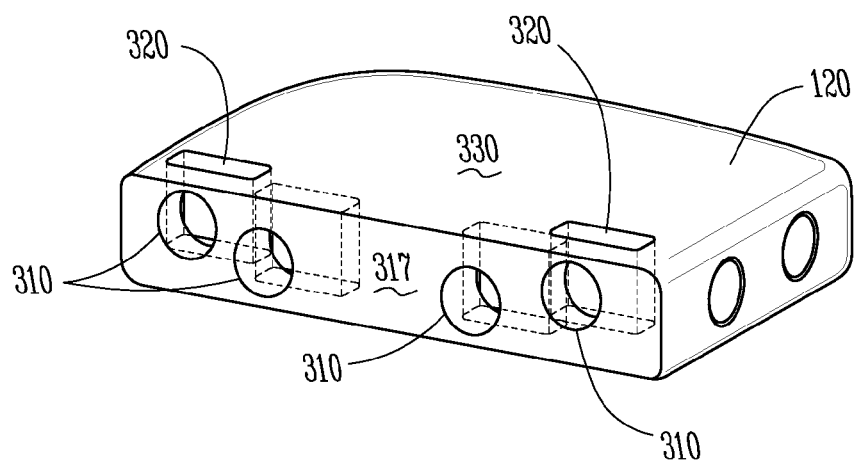
FIG. 3 shows a bottom perspective view of the header of FIG. 2.

FIG. 3 shows a bottom perspective view of the header 120, in accordance with one example. The header 120 includes the one or more cavities 310 located on a bottom surface 317 of the header 120. Each of the cavities 310 extends upwards in the header 120 to communicate with a slot 320. Each slot 320 is open on a side surface 330 of the header 120 and extends inward perpendicularly relative to the cavities 310. The cavities 310, along with the ports 122 and other features of the header 120 are formed when the header 120 is molded.

Figure 4:
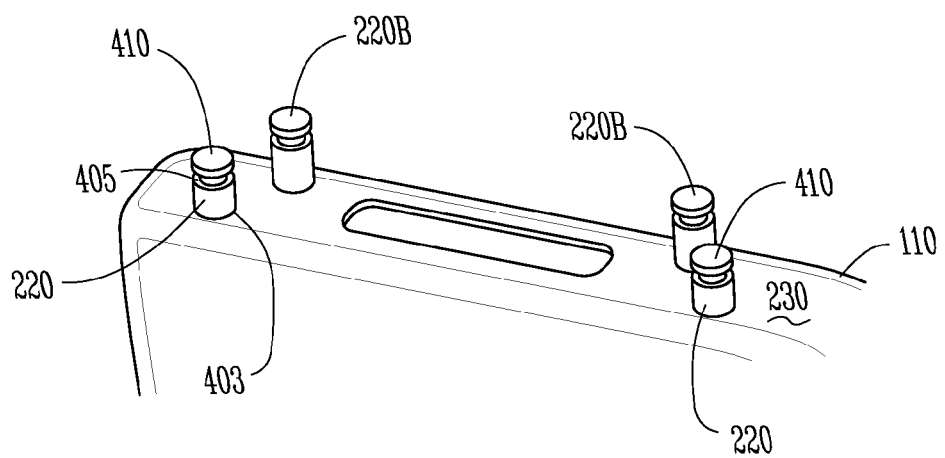
FIG. 4 shows a perspective view of details of a portion of the housing of FIG. 2.

FIG. 4 shows a perspective view of details of the top surface 230 of the housing 110, in accordance with one example. Extending from the top surface 230 are the one or more posts 220. Each of the posts 220 is located so as to matingly enter one of the cavities 310 of the header 120. (See FIG. 3). In this example, each post 220 includes a base portion 403 attached to the top surface 230 of the housing 110, a thinner neck portion 405 dimensioned to receive the retaining members, and an expanded head portion 410. The expanded head portion 410 has a larger cross-sectional surface area than the thinner neck portion 405 so as to hold the retaining member in place.

The posts 220 are mounted to the top surface 230 of the metallic housing 110 by spot welding, for example. In certain examples, the posts 220 can be formed of titanium or stainless steel, or other biocompatible metal that meet a welding and strength requirement. Another consideration is that the metal of posts 220 can be as hard as or harder than the metal of the retaining members 210. (See FIG. 2). This provides that the posts 220 will not deform as the retaining members 210 are being mounted to the posts 220. However, due to other manufacturing concerns such as the bonding of the posts 220 to the housing 110, some examples utilize a metal for the posts 220 that is softer than the metal of retaining members 210. Certain examples use stainless steel 302 or titanium grade 5 for both the posts 220 and retaining members 210.

In one example, posts 220 are staggered relative to each other on the surface of the housing 110. This is for spacing reasons so retaining members 210 do not interfere with each other when the retaining members are mounted to the posts 220. In certain examples, the posts 220 can have different heights. For example, rear posts 220B can be higher than the front posts 220. The height difference between the front posts 220 and the rear posts 220B also helps to keep the retaining members 210 from interfering with each other. The higher level of posts 220B also increases the retention of the header 120 on the housing 110 when lateral forces are applied to the header 120.

Figure 5:
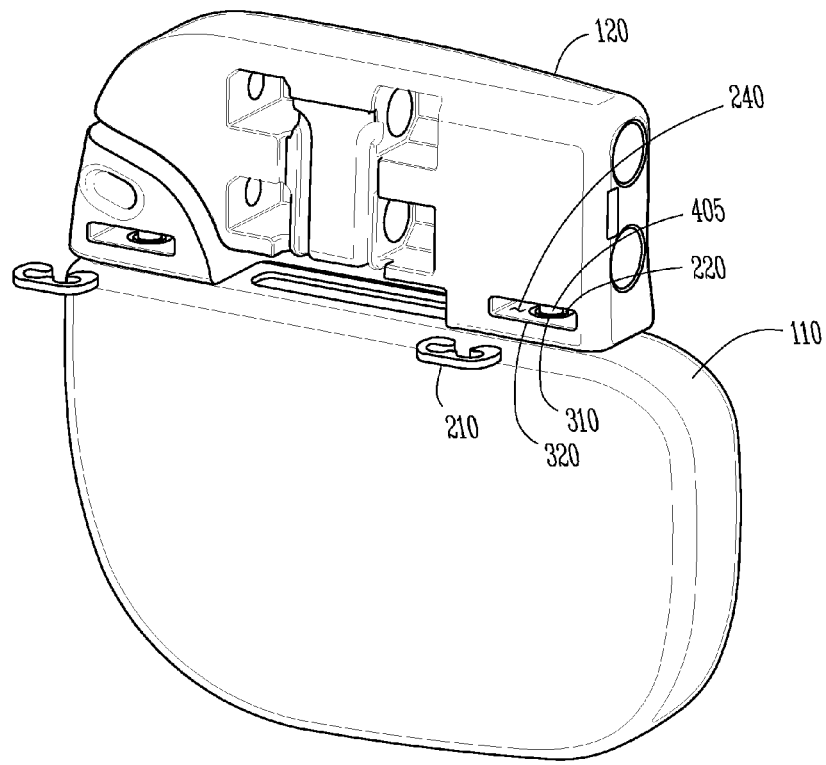
FIG. 5 shows a perspective view of the housing and header of FIG. 2.
Figure 6:
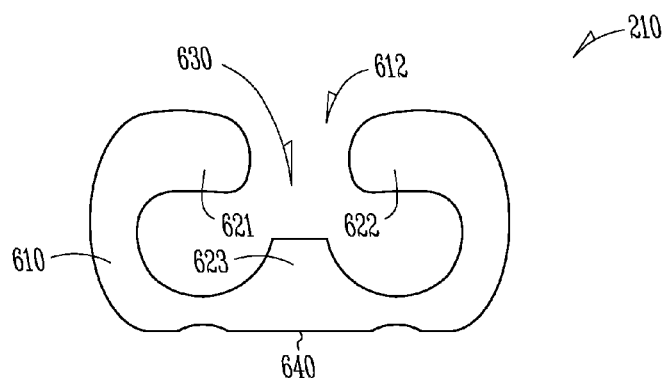
FIG. 6 shows a top view of a retaining member, in accordance with one example.

FIG. 5 shows a perspective view of the header 120 being mounted to the housing 110, and FIG. 6 shows a top view of the retaining member 210, in accordance with one example. In this example, the posts 220 extend into the cavities 310 far enough so that there is enough clearance within the slots 320 for the retaining members 210 to be placed into the slots 320 and mount to the posts 220 with the retaining member under the expanded head portion 410 of the posts 220 (See FIG. 4).

In this example, the retaining members 210 include an external retaining ring, such as an E-ring 610, formed of stainless steel or titanium. The retaining member 210 includes an open side 612 to receive the body of the thinner neck portion 405 of the post 220. Retaining member 210 includes three lobes 621, 622, and 623. A mounting area 630 located between the three lobes 621, 622, and 633 is dimensioned to be slightly smaller than the thinner neck portion 405 of the post 220 so that the retaining member 210 will spring-clip to the post 220 and be retained thereon without falling back off. Retaining member 210 includes a generally flat back surface 640. The flat surface 640 helps prevent any rotation of the retaining member 210 as the retaining member is being mounted to the post 220. For example, a small tool can be used to press against the flat back surface 640 and force the retaining member 210 onto the thinner neck portion 405 of the post 220. If the back surface of the retaining member 210 was round, the retaining member would have a tendency to rotate around the post 220 as it was being pressed from behind. In contrast, the flat back surface 640 helps inhibit such rotation and makes it easier to mount the retaining member 210 to the post 220.

Referring also now to FIG. 2, when the retaining member 210 is mounted to the post 220, the three lobes 621, 622, and 623 provide a retaining surface area by abutting the bottom surface of the expanded head portion 410 of the posts 220 while the bottom surface of the retaining member 210 abuts an internal surface 240 of the bottom of the slot 320.

To mount the header 120 to the housing 110, in accordance with one example, a medical adhesive (not shown) can first be applied between the bottom surface of the header 120 and the top surface 230 of the housing 110. The header 120 is placed onto the housing 110 such that the one or more posts 220 enter their respective cavities 310. The header 120 is pressed down towards the housing 110 until the expanded head portion 410 is above the slot 320 and the thinner neck portion 405 is aligned with the slot 320.

The retaining member 210 is then placed within the slot 320 and pressed further into the slot 320 using a small tool, for example. The retaining member 210 is forced into the slot 320 until the retaining member 210 clips onto the thinner neck portion 405 of the post 220. After all the retaining members have been attached to the posts, pressure is removed from the header 120. Each of the clips 210 then physically helps retain the header 120 on to the housing 110 since the top surface of each retaining member 210 abuts the bottom surface of the expanded head portion 410 of the posts 220 while the bottom surface of the retaining member 210 abuts the internal surface 240 of the bottom of the slot 320.

FIG. 7 shows a perspective view of a header 710, and FIG. 8 shows a top view of a retaining member 720, in accordance with one example. In this example, the one or more retaining members 720 include external retaining rings, such as a push-on retaining ring with internal teeth 810. Retaining members 720 can be used alternatively or additionally to the retaining members 210 discussed above.

Retaining members 720 are circular in shape and include multiple tangs or teeth 823. In certain examples, four teeth 823 are used, defining a mounting area 825 therebetween. Other examples use different number of teeth 823. Retaining members 720 can be formed of stainless steel or titanium for example. Retaining members 720 are inserted into slots 740 in header 710 before the header 710 is mounted to a housing. The header 710 includes cavities 745 on a bottom surface of the header 710. Cavities 745 will mate with corresponding posts on an implantable housing, such as discussed above. Each slot 740 extends perpendicular with and communicates with each cavity 745 such that the retaining member 720 is located within the slot 740 and substantially centered over the cavity 745.

Figure 9:
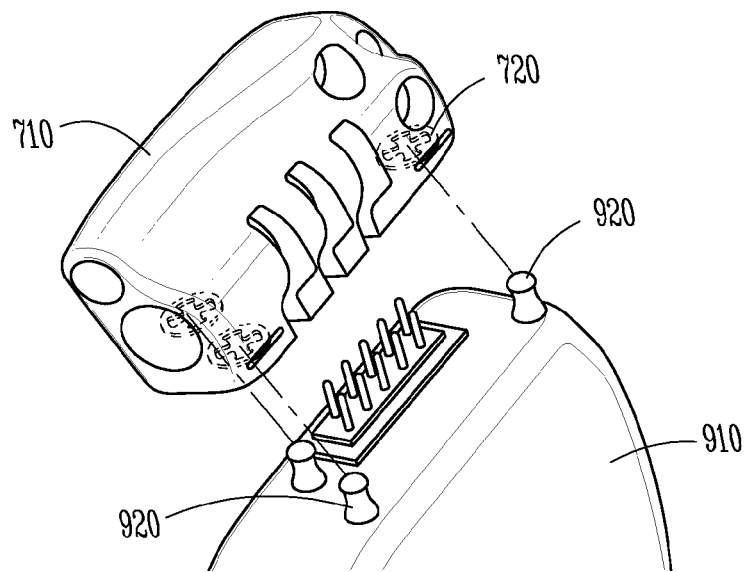
FIG. 9 shows a perspective view of a header and housing, in accordance with one example.
Figure 10:
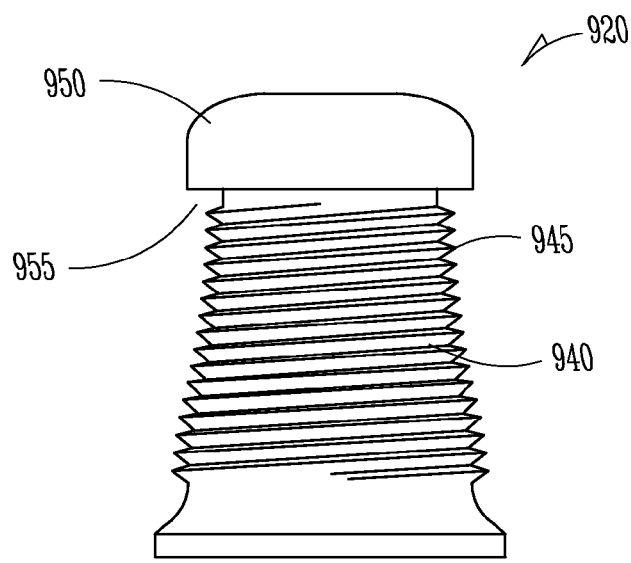
FIG. 10 shows a housing post, in accordance with one example.

FIG. 9 shows a perspective view of the header 710 and a housing 910, and FIG. 10 shows a housing post 920, in accordance with one example. In this example, the posts 920 are metallic posts attached to an upper surface of the housing 910 by welding, for example. Each post 920 includes a body portion 945 including a textured surface, such as a plurality of threads 945. Certain examples use a knurled or tapered post. Each post 920 includes an expanded head portion 950 that has a larger cross-sectional surface area than a thinner neck portion 955.

Figure 11:
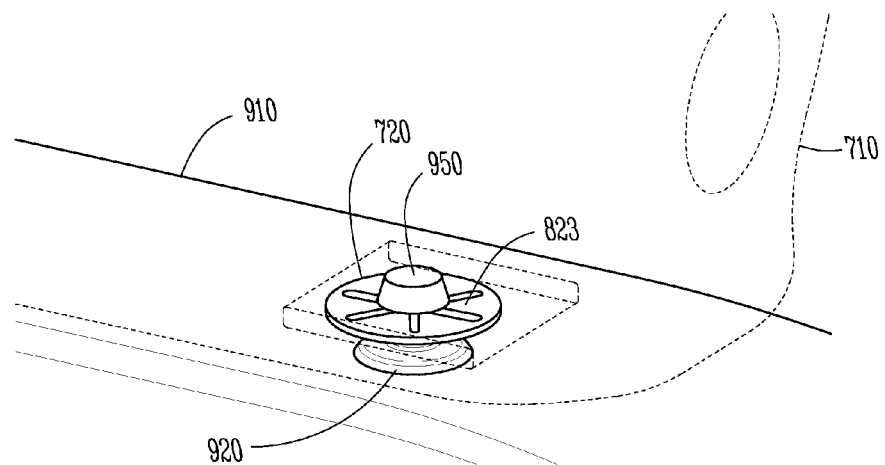
FIG. 11 shows a perspective view of a header and housing, in accordance with one example.

FIG. 11 shows a perspective view of the header 710 mounted to the housing 910, in accordance with one example. The retaining members 720 are pre-assembled into the header 710 by pressing each retaining member 720 into a slot 740. A medical adhesive is applied to the bottom surface of the header 710 and the header 710 is pressed onto the housing 910 using the posts 920, located within cavities 745, as guides until the retaining members 720 are mounted to the posts 920. The teeth 823 of the retaining member 720 deflect over the expanded head portion 950 of the post 920 and then upward movement of the teeth 823 is restricted by the expanded head portion 950 or by the textured side wall surfaces of the post 920. This holds the retaining member 720 in place on the post 920 and since the bottom surface of the retaining member 920 abuts the bottom surface of slot 740 this inhibits movement upward of the header 710 relative to the housing 910. By pre-assembling the retaining members 720 into the slots 740, this manufacturing technique for mounting the header 710 to the housing 910 reduces time for the manufacturing process and saves resources through less labor and higher yield.

In certain examples, the hardness of the post 920 is greater than or equal to the hardness of the retaining member 720 so that the post 920 is not deformed when the retaining member 720 is placed over the expanded head portion 950. However, some examples utilize a metal for the posts 920 that is softer than the metal of retaining members 720. Certain examples use stainless steel 302 or titanium grade 5 for both the posts 920 and retaining members 720.

Figure 12:
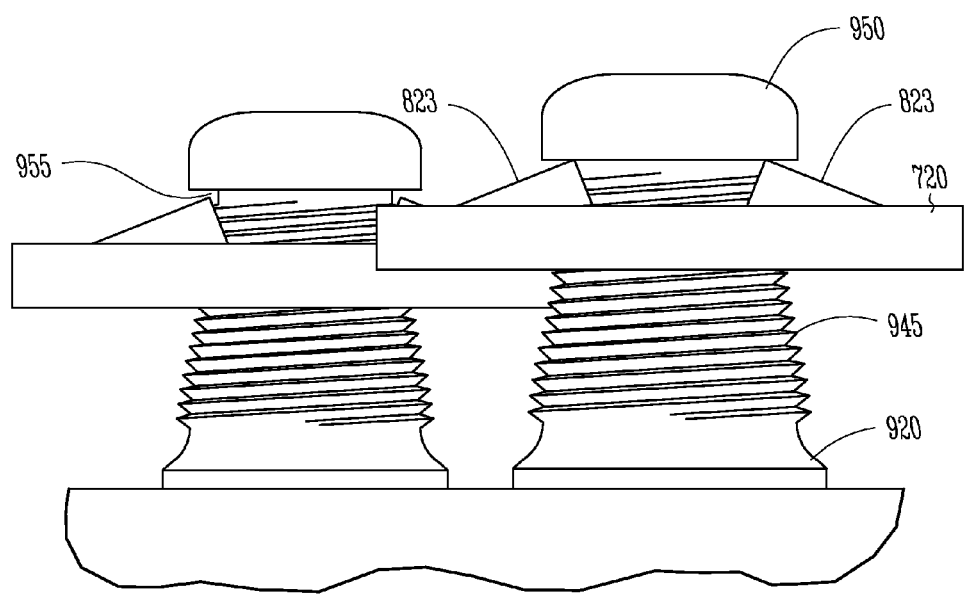
FIG. 12 shows a view of posts and retaining members in accordance with one example.

FIG. 12 shows a view of the retaining member 720 mounted to the post 920 and, in accordance with one example. The retaining member 720 has been pushed over the expanded head portion 950 and some teeth 823 are held in place by the textured surface, such as the threads 945, of the post 920 while other teeth 823 are abutting the bottom surface of the expanded head portion 950 above neck portion 955. Thus, upward movement of the retaining member 720 is restricted by one or more teeth 823 contacting the expanded head portion 950 or by one or more teeth contacting the textured side wall surfaces of the post 920.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus comprising:
an implantable housing;
a header including a cavity;
a post having a post body portion extending from a surface of the housing into the cavity, the post including an expanded head portion larger than the post body portion; and
a retaining member mounted within the header and engaged with the post with a bottom surface of the retaining member abutting an internal surface of the header, wherein the retaining member includes a push-on ring with a plurality of internal teeth pre-loaded into the header before the header is mounted to the post.

2. The apparatus of claim 1, wherein the retaining member includes an external retaining ring.

3. The apparatus of claim 2, wherein the external retaining ring includes an E-ring.

4. The apparatus of claim 2, wherein the post includes external threads.

5. The apparatus of claim 1, including a second post, wherein the first post and the second post have different heights.

6. The apparatus of claim 1, wherein the post is formed of a metallic material and the retaining member is formed of a metallic material and the metallic material of the post is harder than or equal to the hardness of the metallic material of the retaining member.

7. The apparatus of claim 1, wherein a top surface of the retaining member abuts a bottom surface of the expanded head portion.

8. The apparatus of claim 1, wherein the post includes external threads.

9. The apparatus of claim 1, wherein the header includes a slot extending perpendicular with and communicating with the cavity such that the retaining ring is located within the slot to engage the post.

10. An apparatus comprising:
an implantable housing;
a header including one or more ports for receiving a terminal of a medical lead, the header further including a cavity in a bottom surface of the header and a slot in a side surface of the header, where the slot is perpendicular to the cavity and communicates with the cavity;
a post including a post body portion extending from an upper surface of the implantable housing, the post extending into the cavity, the post including an expanded head portion larger than the post body portion; and
a retaining member located within the slot of the header, the retaining member being engaged to the post such that a top surface of the retaining member abuts a bottom surface of the expanded head portion and a bottom surface of the retaining member abutting an internal surface of the header such that the retaining member holds the header against the implantable housing, wherein the retaining member includes a push-on ring with a plurality of internal teeth pre-loaded into the header before the header is mounted to the post.

11. The apparatus of claim 10, wherein the retaining member includes an external retaining ring.

12. The apparatus of claim 11, wherein the external retaining ring includes an E-ring.

13. The apparatus of claim 11, wherein the post is formed of a metallic material and the retaining member is formed of a metallic material and the metallic material of the post is harder than or equal to the hardness of the metallic material of the retaining member.

14. The apparatus of claim 13, wherein the post includes external threads.

15. The apparatus of claim 10, including a second post extending from the upper surface of the implantable housing, wherein the first post and the second post have different heights.

16. A method comprising:
inserting a push-on ring with a plurality of internal teeth into a cavity in a header;
inserting a post attached to an implantable housing into the cavity on the header; and
pushing the push-on ring over the post, with the push-on ring inhibiting movement of the header away from the implantable housing.

17. The method of claim 16, wherein the retaining member includes an external retaining ring.

18. The method of claim 17, wherein the external retaining ring includes an E-ring.

19. The method of claim 17, wherein the post includes external threads.

20. The method of claim 16, wherein the retaining member is mounted to the post such that a top surface of the retaining member abuts a bottom surface of an expanded head portion of the post and a bottom surface of the retaining member abuts an internal surface of the header.

* * * * *